United States Patent [19]
Roberts et al.

[11] Patent Number: 5,440,120
[45] Date of Patent: Aug. 8, 1995

[54] SAMPLING ARRANGEMENT FOR THERMAL GRAVIMETRIC ANALYZER

[75] Inventors: Dean E. Roberts, Deerfield, Wis.; Robert L. Wolfe, Lahabra, Calif.

[73] Assignee: Analytical Technology, Inc., Boston, Mass.

[21] Appl. No.: 223,163

[22] Filed: Apr. 5, 1994

[51] Int. Cl.⁶ .................... H01J 49/00; B01D 59/44
[52] U.S. Cl. ..................................... 250/288; 250/281
[58] Field of Search .................... 250/281, 282, 288

[56] References Cited
U.S. PATENT DOCUMENTS

| | | | |
|---|---|---|---|
| 5,191,211 | 3/1993 | Gorman | 250/282 |
| 5,204,270 | 4/1993 | La Count | 426/157 |
| 5,256,374 | 10/1993 | De Silva et al. | 250/288 |

Primary Examiner—Bruce C. Anderson
Attorney, Agent, or Firm—Emrich & Dithmar

[57] ABSTRACT

A thermal gravimetric analyzer includes a reaction tube disposed within a heating element and including a sample container disposed therein. A reaction gas is introduced at a first end of the reaction tube and allowed to react with the sample, while a purge gas is introduced at a second, opposed end of the reaction tube to isolate a beam system, from which the sample and sample container are suspended, from the reaction gas. A Fourier transform infrared (FTIR) spectrometer as well as a mass spectrometer coupled to the reaction tube may be used to analyze the off-gas products of the reaction of the sample with the reaction gas. Sniffer tubes are used to provide off-gas samples to the two spectrometers, with each sniffer tube having a first inlet end disposed immediately adjacent the sample container and a second outlet end coupled to a sample inlet port of a respective spectrometer. The sniffer tubes increase off-gas product measurement sensitivity by reducing the total volume of gas analyzed and increasing the concentration of the off-gas products within the volume of the gas being analyzed.

13 Claims, 4 Drawing Sheets

SAMPLING ARRANGEMENT FOR THERMAL GRAVIMETRIC ANALYZER

FIELD OF THE INVENTION

This invention relates generally to thermal gravimetric analyzers and is particularly directed to the sampling of the gases produced during reaction in a thermal gravimetric analyzer for spectral analysis.

BACKGROUND OF THE INVENTION

Combined thermogravimetry/mass spectrometry and thermogravimetry/Fourier transform infrared spectroscopy combine the direct measurement of weight loss as a function of reaction temperature with the use of spectroscopic detectors for the qualitative and quantitative determination of evolved volatile products to provide kinetic information about the specific reaction mechanisms. Although offering substantial advances in the areas of detection and analysis, the presence of a component at very low concentrations may be masked by higher concentrations of interferants. Additional steps such as collecting the products in a trap or on the head of a capillary column have been employed for increasing off-gas product detection sensitivity. However, these methods necessarily introduce additional time in the detection/analysis method and result in a loss of the time/temperature evolution data for the products analyzed. Unfortunately, it is frequently most desirable to obtain a time correlation of what is occurring in the reaction of the sample with the reaction gas introduced into the reaction tube.

Another approach to obtaining a time correlation of the reaction process involves increasing the gas flow through the reaction tube while correspondingly increasing the sampling rate. This approach does not compromise the performance of the thermal system or the IR system, and avoids the prior art problems encountered with an excess pressure within the reaction tube which tends to reduce the stability of weight changes of the sample. Unfortunately, this approach renders it more difficult to detect the off-gas products by decreasing the signal-to-noise ratio at the detectors.

The present invention addresses the aforementioned limitations of the prior art by providing a sampling arrangement for a thermal gravimetric analyzer which removes the off-gas products immediately adjacent to the sample holder and provides the thus removed concentrated off-gas products directly to mass and/or IR spectroscopic detectors.

OBJECTS AND SUMMARY OF THE INVENTION

Accordingly, it is an object of the present invention to provide an improved sampling arrangement for the spectral and mass analysis of off-gas products in a thermal gravimetric analyzer.

It is another object of the present invention to enhance detection and measurement sensitivity and accuracy in a thermal gravimetric analyzer by sampling the off-gas products at a location immediately adjacent to the reaction site.

Yet another object of the present invention is to increase detection and measurement sensitivity in a thermal gravimetric analyzer of reaction off-gas products by minimizing dilution of the off-gases by either the reaction gas or a purge gas.

A further object of the present invention is to increase the signal-to-noise ratio in spectrographic apparatus for measuring the interaction between a sample material and its reaction environment.

These objects of the present invention are achieved and the disadvantages of the prior art are avoided by an apparatus for detecting and measuring reaction of a reaction gas with a sample in a thermal gravimetric analyzer including a balance and spectrometer for determining characteristics of an off-gas produced by interaction of the reaction gas and the sample, the apparatus comprising a reactor container for receiving the reaction gas; a cup suspended from the balance and disposed in the reactor container for supporting and maintaining the sample in position in the reactor container; and a sampling arrangement disposed immediately adjacent the cup for receiving off-gas produced by interaction of the sample, temperature and the reaction gas and for providing the off-gas to the spectrometer for analysis.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION OF THE PREFERRED EMBODIMENT

Figure 1:
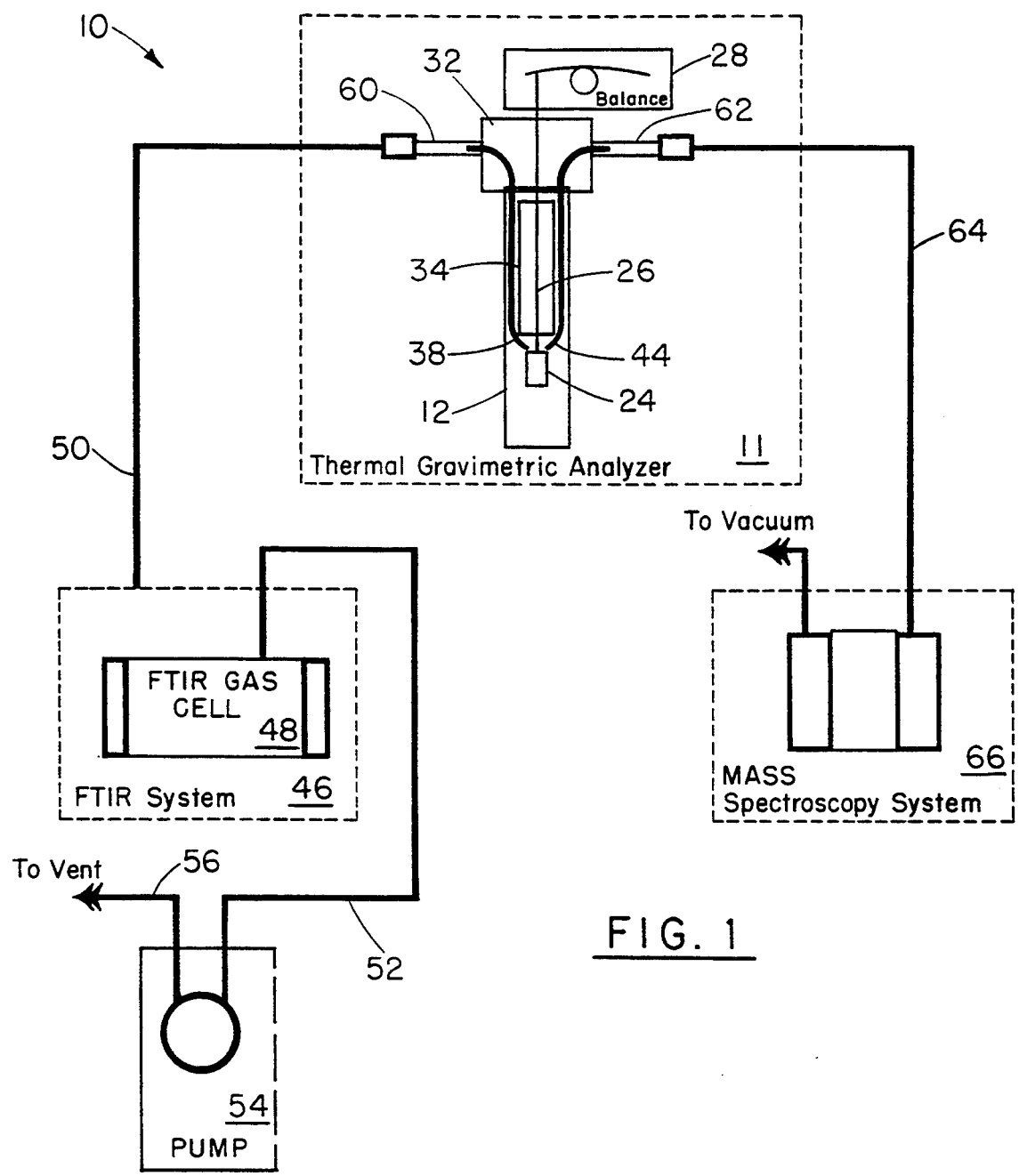
FIG. 1 is a simplified combined schematic and block diagram of a thermal gravimetry/gas chromatography/mass spectrometry system employing a sampling arrangement in accordance with the present invention.
Figure 2:
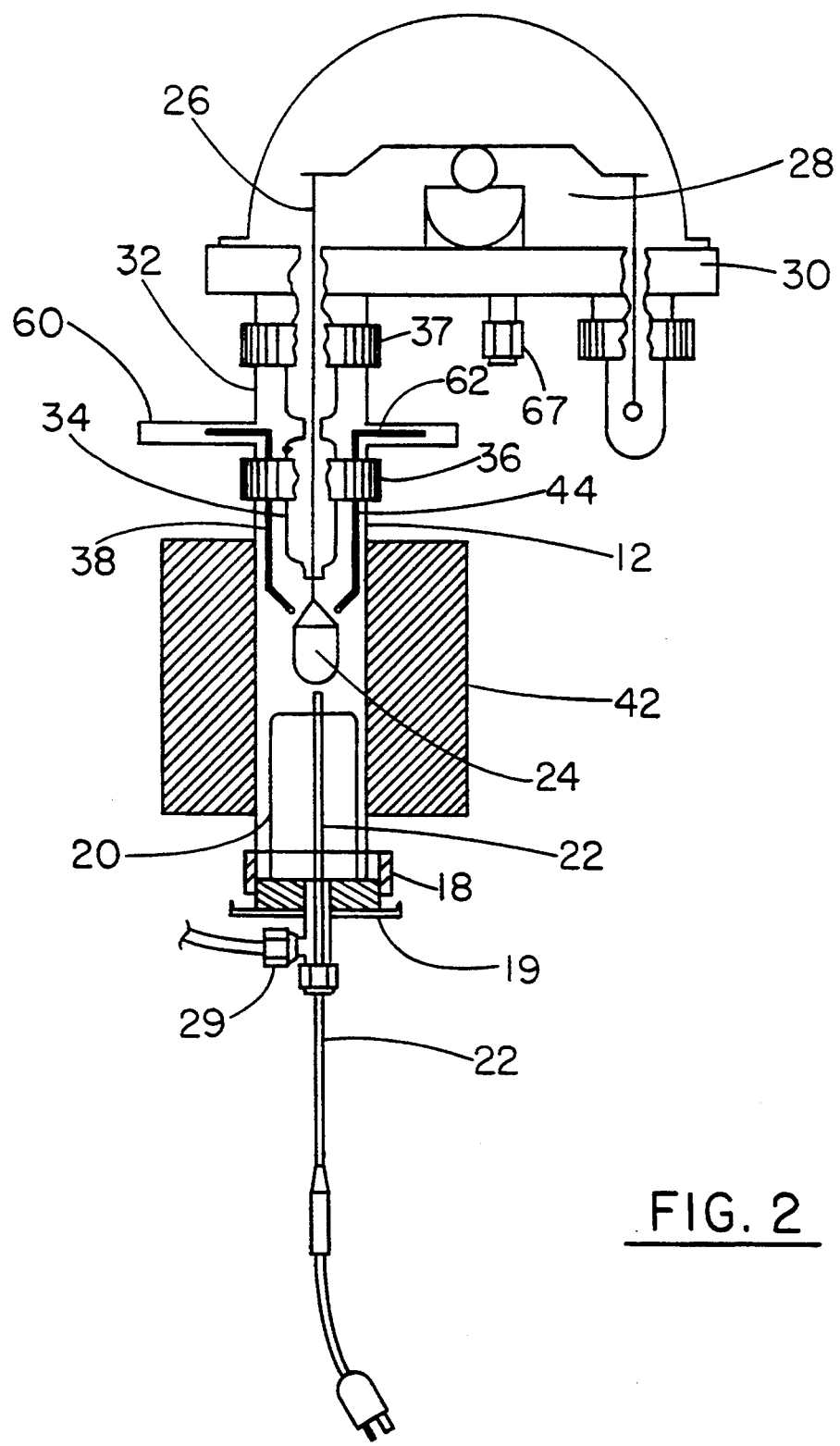
FIG. 2 is a partially cutaway lateral sectional view of a sampling arrangement for a thermal gravimetric analyzer in accordance with the present invention.
Figure 3:
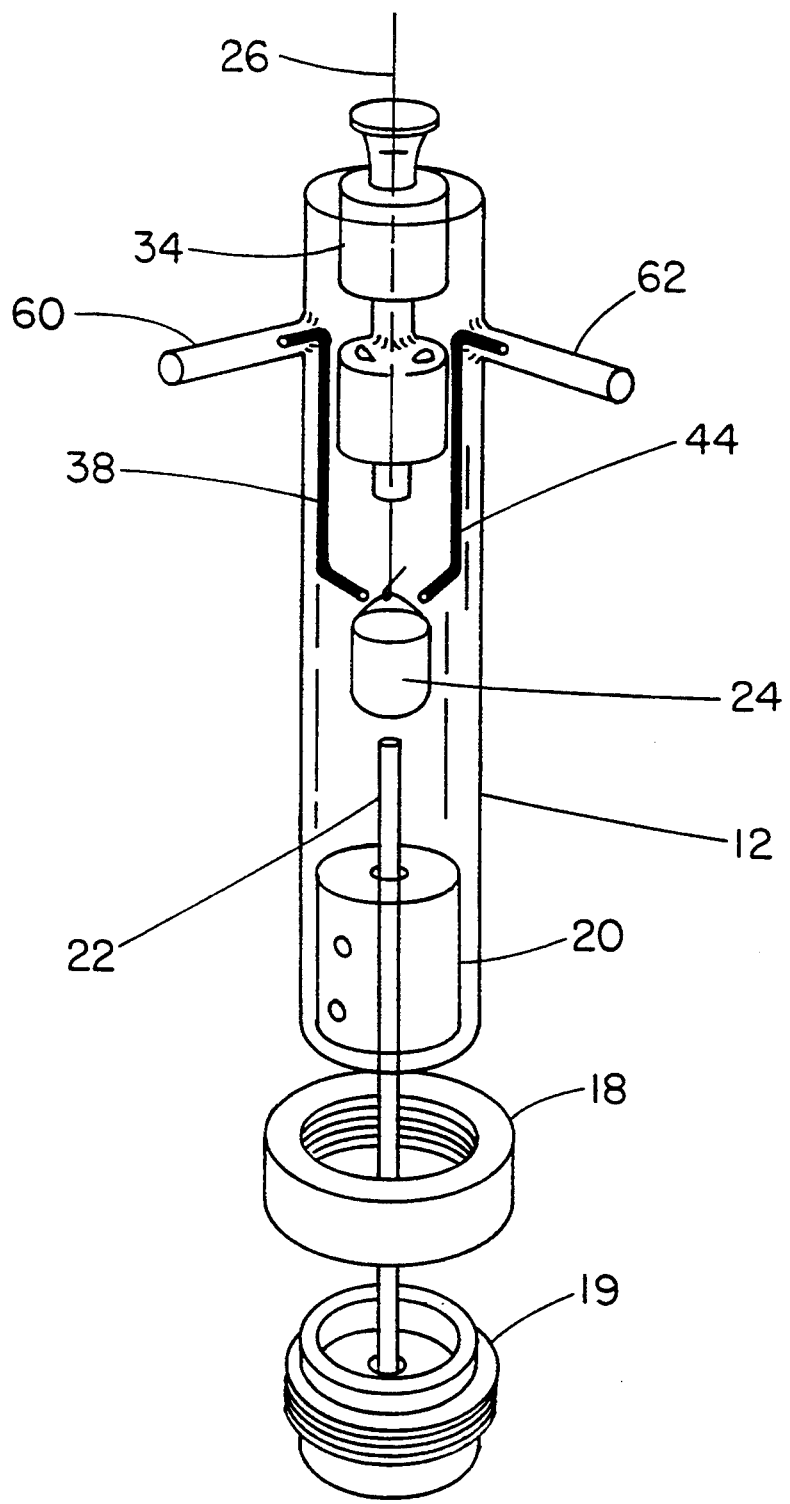
FIG. 3 is a partially exploded perspective view of a reaction tube for a thermal gravimetric analyzer including a sampling arrangement in accordance with the present invention.

Referring to FIG. 1, there is shown a simplified combined schematic and block diagram of a thermogravimetry/gas chromatography/mass spectrometrysystem 10 incorporating a sampling arrangement in accordance with the present invention. The thermogravimetry/gas chromatography/mass spectrometry system 10 includes a thermal gravimetric analyzer 11 including a reactor tube 12 incorporating a sampling arrangement in accordance with the present invention. FIG. 2 is a partially cutaway lateral section view of reactor tube 12, while FIG. 3 is a partially exploded perspective view of the reactor tube incorporated in the thermal gravimetric analyzer 11.

Reactor tube 12 is generally cylindrical and is typically comprised of a hard, rigid, transparent material such as quartz but could be made of nontransparent alumina. Disposed about reactor tube 12 is a heater element 42. Disposed in a lower portion of reactor tube 12 and aligned with its longitudinal axis is a cylindrical volume reducer element 20 which is supported and maintained in position by a lower assembly seal 19 disposed on the lower end of the reactor tube 12. The lower assembly seal 19 is securely maintained in position on the lower end of the reactor tube 12 by means of a first clamp ring, or nut, 18. Extending through an aperture in the lower assembly seal 19 and up into a lower portion of the reactor tube 12 is a thermocouple 22 which provides an indication of the temperature within the reactor tube 12 which is controlled by heater element 42.

Disposed in an upper portion of the reactor tube 12 and aligned along its longitudinal axis is a baffle assembly 34. Baffle assembly 34 and the volume reducer element 20 are also preferably comprised of quartz but could be made of alumina. Baffle assembly 34 includes an elongated aperture extending the length thereof through which an extension wire 26 extends. A lower end of the extension wire 26 is attached to a sample cup 24 which contains the sample of the substance which reacts when temperature is applied and/or a reaction gas introduced into the reactor tube 12. An upper end of the extension wire 26 is coupled to a beam balance 28 for providing the weight of the sample within the sample cup 24 as it reacts with the environment produced within the reaction tube 12. The lower volume reducer element 20 and the upper baffle assembly 34 serve to maintain the concentration of gases highest in the vicinity of the sample in the sample cup 24.

The reaction gas is introduced in a lower portion of the reaction tube 12 via a reaction gas inlet 29 as shown in FIG. 2. An inert purge gas typically comprised of a helium or nitrogen is introduced into an upper portion of the reaction tube 12 via the purge gas inlet 67. The purge gas isolates the beam balance 28 from the reaction gas and thus prevents damage to the beam balance by the reaction gas.

Attached to an upper portion of the reaction tube 12 is an effluent gas adaptor 32. Gas adaptor 32 is coupled in a sealed manner to an upper portion of the reactor tube 12 by means of a second clamped ring 36. Gas adaptor 32 is further coupled in a sealed manner to a lower portion of the beam balance 28 by means of a third clamp ring 37. The effluent gas adaptor 32 includes first and second total flow vent tubes 60 and 62 extending from a lateral wall thereof. The effluent gas adaptor 32 is preferably comprised of an inert, high strength metal such as stainless steel.

In accordance with the present invention, disposed within reactor tube 12 are first and second sniffer tubes 38 and 44. A first, lower end of each of the sniffer tubes 38, 44 is disposed immediately adjacent to, and slightly above, sample cup 24. A second upper end of the first sniffer tube 38 extends into the first total flow vent tube 60. Similarly, a second upper end of the second sniffer tube 44 is disposed in the second flow vent tube 62. Each of the first and second sniffer tubes 38, 44 is comprised of either Iconel, platinum, sapphire or a combination thereof in the disclosed embodiment, platinum being used in high temperature applications with temperatures as high as 1700° C. Each of the first and second sniffer tubes 38, 44 samples the off-gas products immediately adjacent sample cup 24 and provides the sampled off-gas products to the first and second flow vent tubes 60, 62, respectively.

As shown in FIG. 1, coupled to the first total flow vent tube 60 via a first off-gas withdrawal line 50 is an FTIR system 46 including an FTIR gas cell 48. A pump 54 coupled to the FTIR system 46 via a vacuum line 52 draw the off-gas products from the reaction tube 12 via the FTIR system 46. Similarly, coupled to the second sniffer tube 44 via the combination of the second flow vent tube 62 and a second off-gas withdrawal line is a mass spectroscopy system 66. FTIR system 46 provides an infrared spectroscopic analysis of the off-gas products, while the mass spectroscopy system 66 affords a molecular weight analysis of the off-gas products.

Figure 4:
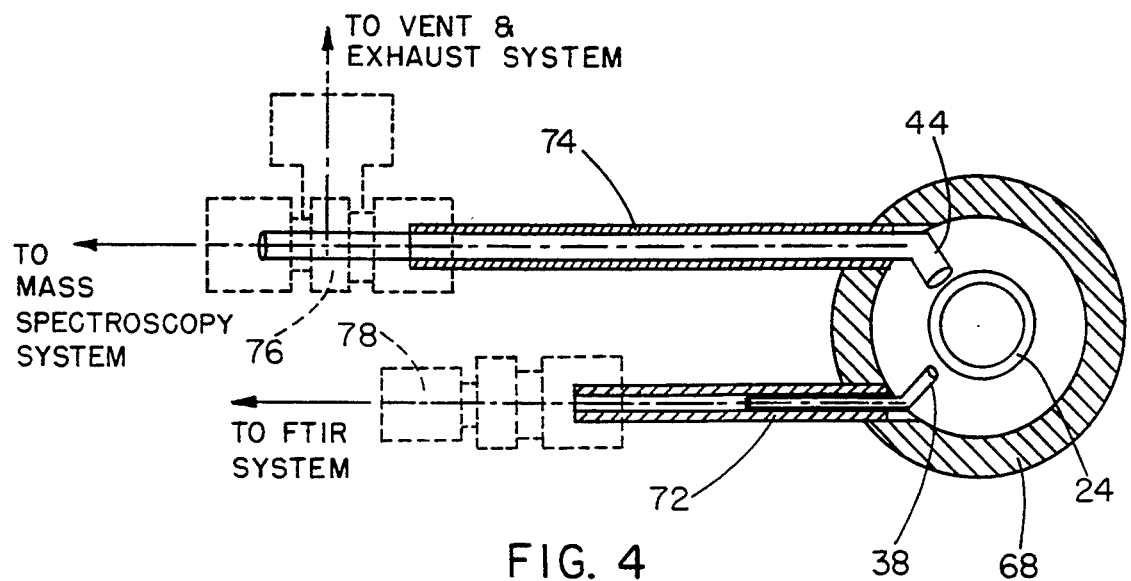
FIG. 4 is a sectional view of an adaptor for a thermal gravimetric analyzer for sampling the off-gas products in accordance with the present invention.

Referring to FIG. 4, there is shown a sectional view of an FTIR adaptor 68 for coupling the inventive sniffer tube 38 to an FTIR system and tube 44 to a mass spectroscopy system. In the embodiment of the FTIR adaptor 68 shown in FIG. 4, the reactor tube containing a sample cup 24 is coupled to both the FTIR system and a mass spectroscopy system as in the previously described embodiment. Attached to and extending from the FTIR adaptor 68 is a sniffer tube vent tube 72 and a total flow vent tube 74. The total flow vent tube 74 encloses and supports the upper end of the sniffer tube 44 and is coupled by means of a tube Tee union 76 (shown in dotted line form) to a vent and exhaust system which is not shown in the figure for simplicity. The sniffer tube vent tube 72 encloses and supports an upper end of sniffer tube 38. The lower ends of sniffer tubes 38 and 44 are positioned immediately adjacent to and slightly above the sample cup 24 as in the previously described embodiment. Both sniffer tubes 38, 44 remove the off-gas products from adjacent the sample cup 24 and provide them to the sniffer vent tubes 72 and 74. The sniffer vent tube 72 is coupled by means of a second tube union 78 (also shown in dotted line form) to an FTIR system (also not shown for simplicity) for spectral analysis of the off-gas products. The vent and exhaust system ensures an upward flow of the off-gas products within the reaction tube for delivery of the FTIR system for analysis.

Figure 5:
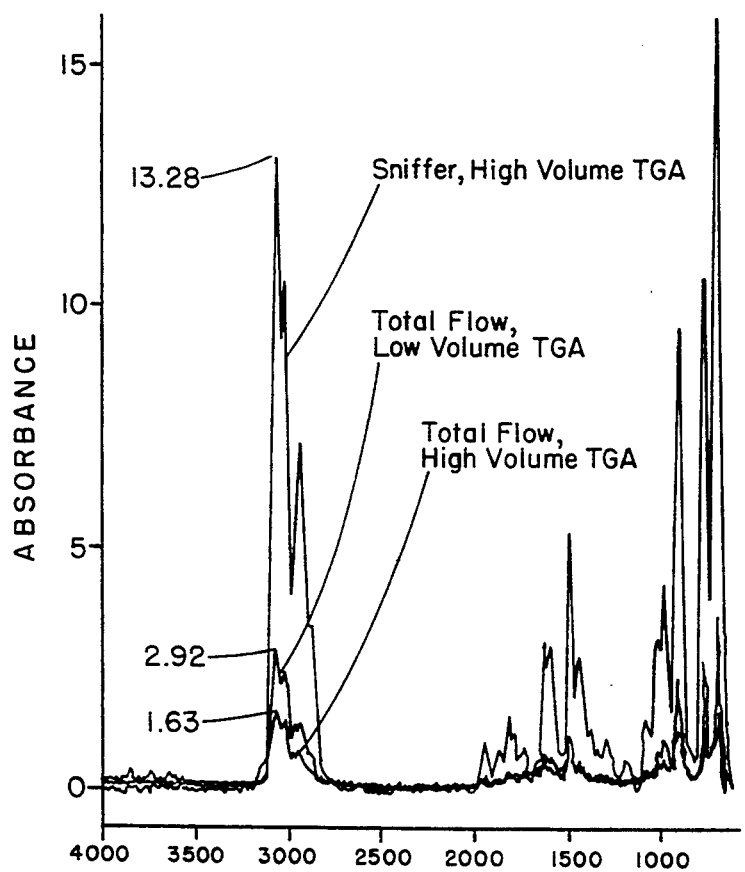
FIG. 5 is a graphic comparison of the sensitivity in measuring off-gas products using the sampling arrangement of the present invention with prior art approaches.

Referring to FIG. 5, there is shown a graphic comparison of the sensitivity in measuring off-gas products using the sampling arrangement of the present invention with prior art approaches. From the figure, it can be seen that at 3000 wavenumbers, the lowest curve labeled Total Flow, High Volume TGA indicates an absorbance of 1.63. This curve represents the measured results at a gas flow rate of 140 ml/min. These high gas dilutions decrease the signal to background noise ratio so as to mask the absorbance by the off-gas products and reduce measurement sensitivity. The next higher curve is labeled Total Flow, Low Volume TGA for a flow rate of 35 ml/min. This relatively low absorbance signal is due to the smaller volume of the gas being sampled. The Total Flow, Low Volume TGA curve shows an absorbance value of 2.92 at 3000 wavenumbers. Finally, the uppermost curve labeled Sniffer, High Volume TGA shows a substantial increase in the measured absorbance at a value of 13.28 at 3000 wavenumbers. This latter absorbance curve was derived using a sniffer tube in accordance with the present invention at a flow rate of 140 ml/min and indicates a sensitivity increase of an order of magnitude (10×) using the sampling arrangement of the present invention. The increased sensitivity of a sampling arrangement utilizing the sniffer tube of the present invention allows for a relaxation in the performance requirements of the detectors used in the chromatographic or mass spectroscopy system.

There has thus been shown a sampling arrangement for use in a thermal gravimetric analyzer which substantially increases detection sensitivity of the off-gas products within the analyzer's reaction tube. By sampling the off-gas products immediately adjacent the sample container, the concentration of the off-gas sample is substantially increased allowing for a reduction in the volume of the gas analyzed and a relaxation in the sensitivity of the detectors in the detection and measuring apparatus.

While particular embodiments of the present invention have been shown and described, it will be obvious to those skilled in the art that changes and modifications may be made without departing from the invention in its broader aspects. Therefore, the aim in the appended claims is to cover all such changes and modifications as that which falls within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. Apparatus for detecting and measuring reaction of a reaction gas with a sample in a thermal gravimetric analyzer including a balance and a spectrometer for determining characteristics of an off-gas produced by interaction of said reaction gas and said sample, said apparatus comprising:

a reactor container for receiving the reaction gas;

cup means suspended from the balance and disposed in said reactor container for supporting and maintaining the sample in position in said reactor container; and sampling means disposed immediately adjacent said cup means for receiving off-gas produced by interaction of the sample and the reaction gas and for providing said off-gas to the spectrometer for analysis.

2. The apparatus of claim 1 wherein said sampling means includes an elongated, hollow tube having a first end disposed immediately adjacent said cup means and a second, opposed end coupled to the spectrometer.

3. The apparatus of claim 2 wherein said tube is Iconel.

4. The apparatus of claim 2 wherein said tube is platinum.

5. The apparatus of claim 2 wherein said tube is sapphire.

6. The apparatus of claim 2 further comprising an adapter coupled to said tube and said reactor container for passing said tube into said reactor container in a sealed manner.

7. The apparatus of claim 6 wherein said adapter is stainless steel.

8. The apparatus of claim 6 further comprising a discharge duct extending through said adapter and into said reactor container for removing the reaction gas and a purge gas from said reactor container.

9. The apparatus of claim 8 wherein said adapter and said discharge duct are disposed downstream of said cup means relative to a flow of said reaction gas.

10. The apparatus of claim 1 wherein said spectrometer includes a Fourier transform infrared (FTIR) spectrometer and a mass spectrometer, and wherein said sampling means includes first and second elongated, hollow tubes, and wherein each of said first and second tubes has a respective first end disposed immediately adjacent said cup means and a respective second, opposed end coupled to said FTIR spectrometer and to said mass spectrometer, respectively.

11. The apparatus of claim 1 further comprising a heating element for heating said cup means and the sample therein.

12. The apparatus of claim 11 wherein said heating element is disposed about said reactor container and adjacent said cup means.

13. Apparatus for detecting and measuring reaction of a reaction gas with a sample in a thermal gravimetric analyzer including a balance and a spectrometer for determining characteristics of an off-gas produced by interaction of said reaction gas and said sample, said apparatus comprising:

a reactor container for receiving the reaction gas;

cup means suspended from the balance and disposed in said reactor container for supporting and maintaining the sample in position in said reactor container; and an elongated sampling tube disposed in said reactor container and having a first end disposed immediately adjacent said cup means and a second, opposed end coupled to said spectrometer for providing the off-gas produced in said cup means by interaction of said reaction gas and said sample to said spectrometer.

* * * * *

UNITED STATES PATENT AND TRADEMARK OFFICE
CERTIFICATE OF CORRECTION

PATENT NO. : 5,440,120
DATED : August 8, 1995
INVENTOR(S) : Dean E. Roberts and Robert L. Wolfe It is certified that error appears in the above-indentified patent and that said Letters Patent is hereby corrected as shown below:

In column 2, line 54, at the beginning of the line where the letters "rysystem" are, there should be a space and the line should begin --ry system--.

Signed and Sealed this

Twenty-fourth Day of October, 1995

Attest:

BRUCE LEHMAN

*Attesting Officer*           *Commissioner of Patents and Trademarks*